United States Patent [19]

Kurusu et al.

[11] Patent Number: 5,439,676
[45] Date of Patent: Aug. 8, 1995

[54] CAMP DERIVATIVES AND USE THEREOF FOR PREVENTING OR RESTORING GRAYED HAIR TO ITS NATURAL COLOR

[75] Inventors: Keiji Kurusu, Odawara; Yoshiyuki Watanabe, Matsudo; Keikichi Sugiyama, Kanagawa; Akira Kiyomiya, Matsudo, all of Japan

[73] Assignee: Lion Corporation, Tokyo, Japan

[21] Appl. No.: 186,247

[22] Filed: Jan. 25, 1994

Related U.S. Application Data

[63] Continuation of Ser. No. 631,478, Dec. 21, 1990, abandoned.

[30] Foreign Application Priority Data

Dec. 27, 1989 [JP] Japan ................................. 1-339709

[51] Int. Cl.$^6$ ................................. A61K 7/06
[52] U.S. Cl. ................................. 424/70.6; 132/202; 514/937; 514/944; 514/945; 514/880
[58] Field of Search ................. 424/70, 71, 70.6, 70.2; 132/202; 514/944, 945, 937, 880

[56] References Cited

FOREIGN PATENT DOCUMENTS

| | | |
|---|---|---|
| 260697 | 3/1988 | European Pat. Off. . |
| 332847 | 9/1989 | European Pat. Off. . |
| 2077725 | 5/1971 | France . |
| 60-17470 | 9/1985 | Japan . |
| 61-16531 | 7/1986 | Japan . |
| 62-04552 | 2/1987 | Japan . |
| 62-06350 | 3/1987 | Japan . |
| 62-06351 | 3/1987 | Japan . |
| 0332847 | 9/1989 | Japan . |
| 2151924 | 7/1985 | United Kingdom . |

*Primary Examiner*—Raj Bawa
*Attorney, Agent, or Firm*—Burns, Doane, Swecker & Mathis

[57] ABSTRACT

Methods and compositions containing cAMP salts in combination with inert carriers for preventing or restoring grayed hair to its natural color.

11 Claims, No Drawings

CAMP DERIVATIVES AND USE THEREOF FOR PREVENTING OR RESTORING GRAYED HAIR TO ITS NATURAL COLOR

This application is a continuation of application Ser. No. 07/631,478, filed Dec. 21, 1990, now abandoned.

BACKGROUND OF THE INVENTION

The present invention relates to a composition for hair which, upon application to the scalp, activates melanocytes of the radix pili and promotes synthesis of melanin, thereby preventing graying of hair and restoring grayed hair to its natural color.

Graying of hair is a universal aging phenomenon. While hair dyes have been commonly used to dye grayed hair from the viewpoint of beauty, the use of such dyes is troublesome and sometimes causes side-effects such as rash of the scalp. Therefore, many users find hair dyes to be an unsatisfactory solution of the graying of the hair.

Under such circumstances, it has been desired to develop a pharmaceutical preparation or a cosmetic composition for application to hair capable of essentially preventing graying of hair and restoring grayed hair to its natural color.

There have been some proposals heretofore such as those described in Japanese Patent Unexamined Publication (hereinafter referred to as "J.P. KOKAI") Nos. 60-174705, 61-165310, 62-45527, 62-63509 and 62-63510 in compliance with such a demand. However, the proposed techniques suffer from various disadvantages such as low effectiveness, low stability of the active components and insufficient safety. Thus no practically satisfactory composition can be obtained at present.

The inventors previously completed an invention based on a finding that the above-described problems can be effectively solved by incorporating a specified nucleic acid compound or a derivative thereof which is contained in a very small amount in the tissues and cells in the living organisms and which has various regulating functions and physiological effects into a cosmetic base (J.P. KOKAI Nos. 63-183518 and 64-25712). However, the effects of such a compound are yet unsatisfactory, since the absorbability thereof through the scalp is insufficient.

Summary of the Invention

Accordingly, a primary object of the present invention is to provide a practically useful composition for hair which, upon application to the scalp, can exhibit remarkable effects of preventing graying of hair and restoring grayed hair to its natural color, since it has an effect of improving the absorbability of the effective component through the scalp.

Another object of the present invention is to provide a method for preventing graying of hair and restoring grayed hair to its natural color.

These and other objects of the present invention will be apparent from the following description and Examples.

The present invention has been completed on the basis of a finding that the absorbability of the effective component through the scalp can be improved by incorporating adenosine 3′,5′-cyclic phosphoric acid (hereinafter referred to as "cAMP") derivative which is a specific nucleic acid compound in the form of a specific salt thereof into a cosmetic base and that the absorbability thereof through the scalp can be further improved by incorporating a specific nonionic or anionic surfactant thereinto and, therefore, the foregoing objects of the present invention can be effectively achieved.

The present invention provides a composition for hair comprising a salt of the following formula [I] or [II] and an inert carrier;

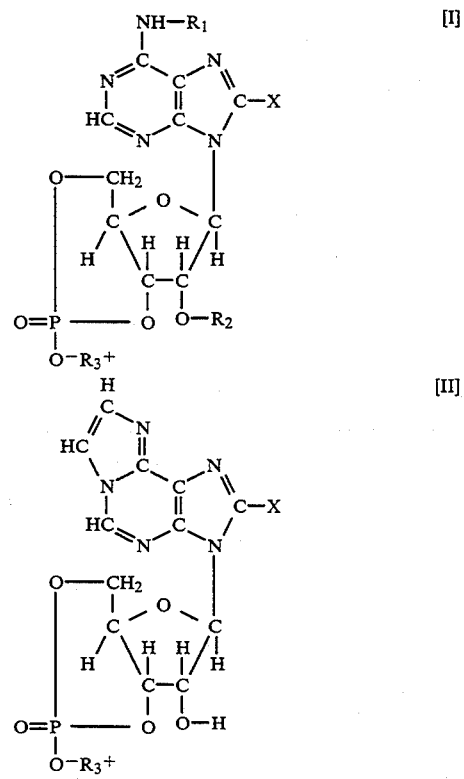

wherein $R_1$ and $R_2$ each represent a hydrogen atom or an acyl group having 1 to 12 carbon atoms, X represents a hydrogen atom, an O-containing group, a S-containing group, an alkylamino group having 1 to 12 carbon atoms or a halogen atom, and $R^+_3$ represents an ammonium cation derived from 2-amino-2-methyl-1,3-propanediol, 2-amino-1-alkanol having 3 to 6 carbon atoms, monoalkylamine having 1 to 3 carbon atoms, lysine or histidine. The present invention also provides a composition for hair, comprising [A] the salt represented by formulas [I] or [II], [B] a nonionic surfactant having an HLB in the range of 3 to 19 or phosphoric ester-type anionic surfactant and [C] an inert carrier.

DESCRIPTION OF THE PREFERRED EMBODIMENTS

In the above formulae, [I] and [II]; $R_1$ and $R_2$ each represent a hydrogen atom or an acyl group having 1 to 12 carbon atoms, preferably 1 to 6 carbon atoms, X represents a hydrogen atom, a halogen atom such as bromine, iodine, chlorine or fluorine, an O-containing group such as a hydroxyl group, an -o-alkyl group having 1 to 12, preferably 1 to 6 carbon atoms, -o-phenyl group or a phenylalkyleneoxy group in which the alkylene group has 1 to 6 carbon atoms, preferably 1 to 4 carbon atoms, an S-containing group such as a mercapto group, an alkylthio group or hydroxyalkylthio group having 1 to 12 carbon atoms, preferably 1 to 4 carbon atoms, a phenylthio group, a halogenated phenylthio group such as chlorinated or brominated phenylthio group, a hydroxyphenylthio group, an alkylphenylthio group in which the alkyl group has 1 to 6 carbon atoms, preferably 1 to 4 carbon atoms, an alkoxyphenylthio group wherein the alkoxyl group has 1 to 6 carbon atoms or an aromatic thio group such as a phenylalkylenethio group wherein the alkylene group has 1 to 6, preferably 1 to 4 carbon atoms, e.g. benzylthio group or phenethylthio group, or an alkylamino group having 1 to 12 carbon atoms, preferably 1 to 4 carbon atoms.

The acyl group and alkyl group may be either saturated or unsaturated and straight chain or branched one. It may have a substituent such as a halogen atom, an amino group, a nitro group, a carboxyl group or a hydroxyl group and it may have an aromatic ring. The acyl group may be derived from a dibasic acid.

$R_3^+$ represents an ammonium cation derived from 2-amino-2-methyl-1,3-propanediol, 2-amino-1-alkanol having 3 to 6 carbon atoms, preferably 2-amino-2-methyl-1-propanol, 2-amino-1-propanol, 2-amino-1-hexanol, monoalkylamine having 1 to 3 carbon atoms, preferably methylamine, lysine or histidine.

The compound of the general formula [I] or [II] is a compound shown in Table 1 or a mixture of two or more of these compounds.

In Table 1, AMP and AMPD represent an ammonium cation derived from 2-amino-2-methyl-1-propanol and 2-amino-2-methyl-1,3-propanediol, respectively.

TABLE 1

| No. | formula | $R_1$ | $R_2$ | X | $R_3$ |
|---|---|---|---|---|---|
| 1 | [I] | H | H | H | AMP |
| 2 | | $COCH_3$ | H | H | AMP |
| 3 | | $COC_3H_7$ | H | H | AMP |
| 4 | | $COC_2H_4CO_2H$ | H | H | AMP |
| 5 | | H | $COCH_3$ | H | AMP |
| 6 | | H | $COC_3H_7$ | H | AMP |
| 7 | | H | $COC_3H_7$ | Br | AMP |
| 8 | | $COCH_3$ | $COCH_3$ | H | AMP |
| 9 | | $COC_3H_7$ | $COC_3H_7$ | H | AMP |
| 10 | | $COC_2H_4CO_2H$ | $COC_2H_4CO_2H$ | H | AMP |
| 11 | | H | H | Br | AMP |
| 12 | | H | H | I | AMP |
| 13 | | H | H | Cl | AMP |
| 14 | | H | H | F | AMP |
| 15 | | H | H | OH | AMP |
| 16 | | H | H | $OCH_3$ | AMP |
| 17 | | H | H | $OC_2H_5$ | AMP |
| 18 | | H | H | $OC_4H_9$ | AMP |
| 19 | | H | H | $OC_6H_{13}$ | AMP |
| 20 | | H | H | 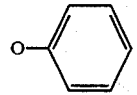 | AMP |
| 21 | | H | H | 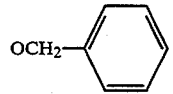 | AMP |
| 22 | | H | H | 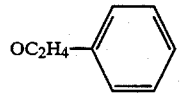 | AMP |
| 23 | | H | H | SH | AMP |
| 24 | | H | H | $SCH_3$ | AMP |
| 25 | | H | H | $SC_2H_5$ | AMP |
| 26 | | H | H | $SC_4H_9$ | AMP |
| 27 | | H | H | $SC_2H_4OH$ | AMP |
| 28 | | H | H | 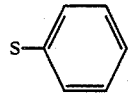 | AMP |
| 29 | | H | H |  | AMP |
| 30 | | H | H |  | AMP |

TABLE 1-continued

| No. | formula | R₁ | R₂ | X | R₃ |
|---|---|---|---|---|---|
| 31 | | H | H | 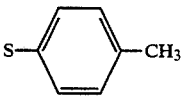 S—⟨C₆H₄⟩—CH₃ | AMP |
| 32 | | H | H | 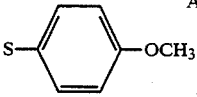 S—⟨C₆H₄⟩—OCH₃ | AMP |
| 33 | | H | H | 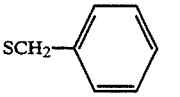 SCH₂—⟨C₆H₅⟩ | AMP |
| 34 | | H | H | 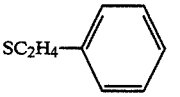 SC₂H₄—⟨C₆H₅⟩ | AMP |
| 35 | | H | H | NHCH₃ | AMP |
| 36 | | H | H | NHC₂H₅ | AMP |
| 37 | | H | H | NHC₄H₉ | AMP |
| 38 | | H | H | H | AMPD |
| 39 | | COCH₃ | H | H | AMPD |
| 40 | | COC₃H₇ | H | H | AMPD |
| 41 | | COC₂H₄CO₂H | H | H | AMPD |
| 42 | | H | COCH₃ | H | AMPD |
| 43 | | H | COC₃H₇ | H | AMPD |
| 44 | | H | COC₃H₇ | Br | AMPD |
| 45 | | COCH₃ | COCH₃ | H | AMPD |
| 46 | | COC₃H₇ | COC₃H₇ | H | AMPD |
| 47 | | COC₂H₄CO₂H | COC₂H₄CO₂H | H | AMPD |
| 48 | | H | H | Br | AMPD |
| 49 | | H | H | I | AMPD |
| 50 | | H | H | Cl | AMPD |
| 51 | | H | H | F | AMPD |
| 52 | | H | H | OH | AMPD |
| 53 | | H | H | OCH₃ | AMPD |
| 54 | | H | H | OC₂H₅ | AMPD |
| 55 | | H | H | OC₄H₉ | AMPD |
| 56 | | H | H | OC₆H₁₃ | AMPD |
| 57 | | H | H |  O—⟨C₆H₅⟩ | AMPD |
| 58 | | H | H | 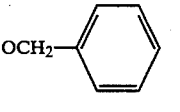 OCH₂—⟨C₆H₅⟩ | AMPD |
| 59 | | H | H | 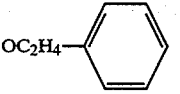 OC₂H₄—⟨C₆H₅⟩ | AMPD |
| 60 | | H | H | SH | AMPD |
| 61 | | H | H | SCH₃ | AMPD |
| 62 | | H | H | SC₂H₅ | AMPD |
| 63 | | H | H | SC₄H₉ | AMPD |
| 64 | | H | H | SC₂H₄OH | AMPD |
| 65 | | H | H |  S—⟨C₆H₅⟩ | AMPD |

TABLE 1-continued

| No. | formula | R₁ | R₂ | X | R₃ |
|-----|---------|----|----|---|----|
| 66 | | H | H | S—C₆H₄—Cl | AMPD |
| 67 | | H | H | S—C₆H₄—OH | AMPD |
| 68 | | H | H | S—C₆H₄—CH₃ | AMPD |
| 69 | | H | H | S—C₆H₄—OCH₃ | AMPD |
| 70 | | H | H | SCH₂—C₆H₅ | AMPD |
| 71 | | H | H | SC₂H₄—C₆H₅ | AMPD |
| 72 | | H | H | NHCH₃ | AMPD |
| 73 | | H | H | NHC₂H₅ | AMPD |
| 74 | | H | H | NHC₄H₉ | AMPD |
| 75 | [II] | | | H | AMP |
| 76 | | | | Cl | AMP |
| 77 | | | | OH | AMP |
| 78 | | | | OCH₃ | AMP |
| 79 | | | | SC₄H₉ | AMP |
| 80 | | | | SCH₂—C₆H₅ | AMP |
| 81 | | | | NHC₄H₉ | AMP |
| 82 | | | | H | AMPD |
| 83 | | | | Cl | AMPD |
| 84 | | | | OH | AMPD |
| 85 | | | | OCH₃ | AMPD |
| 86 | | | | SC₄H₉ | AMPD |
| 87 | | | | SCH₂—C₆H₅ | AMPD |
| 88 | | | | NHC₄H₉ | AMPD |

Further, examples of the salt represented by formula [I] or [II] include 2-amino-1-propanol salt, 2-amino-1-butanol salt, 2-amino-1-pentanol salt, 2-amino-1-hexanol salt, lysine salt, histidine salt, methylamine salt, ethylamine salt, propylamine salt of cAMP and derivatives thereof shown in Table 1, No. 1-88 and a mixture thereof.

The cAMP derivatives used in the present invention can be prepared by a chemical synthesis using, as a starting material, cAMP which has been produced by fermentation methods or synthetic methods on an industrial scale.

Among the inert carriers which may be employed in accordance with the present invention are water and a lower alcohol such as ethanol and isopropanol.

According to the present invention, the compound [A] is directly applied to the scalp alone or in combination with a compound [B] which will be described below to exhibit an excellent effect of preventing graying of hair and restoring grayed hair to its natural color. The concentration of the compound [A] in the composition is not particularly limited. The concentration of the compound [A] in the composition which varies depending on the form of the preparation and frequency of the use thereof is usually about 0.001 to 5% by weight (hereinafter referred to as "%" for simplicity), preferably 0.01 to 2%, based on the total weight of the composition.

The component [B] used in the present invention is a nonionic surfactant having an HLB in the range of 3 to 19 or a phosphoric ester-type anionic surfactant. When HLB is not within this range, the absorbability of the physiologically active nucleic acid derivative [A] through the scalp cannot be improved. Preferably a nonionic surfactant having an HLB in the range of 5 to 18 or anionic surfactant of a type of sodium salt of phosphoric ester is used.

Examples of the components [B] include ether type nonionic surfactants such as polyoxyethylene derivatives of higher alcohols (including primary or secondary, straight chain or branched, and saturated or unsaturated higher alcohols) and polyoxyethylene derivatives of alkylphenols; and ester-type nonionic surfactants such as polyoxyethylene higher fatty acid esters, polyoxyethyleneglyceryl higher fatty acid esters, polyoxyethylene sorbitan higher fatty acid esters, polyoxyethylene sorbitol higher fatty acid esters, polyoxyethylene trimethylolpropane higher fatty acid esters, polyoxyethylene derivatives of hardened castor oil, polyoxyethylene hardened castor oil/higher fatty acid esters, glycerol higher fatty acid esters and sorbitan higher fatty acid esters. Examples of the components [B] also include phosphoric ester type anionic surfactants such as sodium phosphate salts of polyoxyethylene derivatives of higher alcohols (including primary or secondary, straight chain or branched, and saturated or unsaturated higher alcohols).

Among the above-described nonionic surfactants, particularly preferred are ether-type polyoxyethylene derivatves of higher alcohols (including primary or secondary, straight chain or branched, and saturated or unsaturated higher alcohols). Desirably, the higher alcohols have 8 to 24 carbon atoms and the average addition molar number of ethylene oxide is 2 to 40.

Among the phosphoric ester-type anionic surfactants, particularly preferred are sodium phosphate salts of polyoxyethylene derivatives of higher alcohols (including primary or secondary, straight chain or branched, and saturated or unsaturated higher alcohols) in which the higher alcohol has 12 to 18 carbon atoms and which has an average ethylene oxide addition molar number of 1 to 20.

The concentration of the compound [B] in the composition for hair is not particularly limited. The concentration of the compound [B] in the composition, which varies depending on the form of the preparation and frequency of the use thereof is usually about 0.1 to 20% by weight, preferably 0.3 to 10%, based on the total weight of the composition. When it is less than 0.1%, the sufficient effect of improving the absorbability of the effective component [A] through the scalp cannot be obtained and, on the other hand, when it exceeds 20% by weight, the composition becomes too much sticky to obtain a comfortable feeling upon use.

The ratio of the component [A] to the component [B] is not limited. However, the weight ratio of the component [A] to the component [B] is usually 1/2000 to 50/1, preferably 1/500 to 20/1.

In addition to the foregoing components, the composition of the present invention may further contain other pharmaceutical components such as vitamins, e.g. vitamin A, vitamin $B_6$, vitamin E, pantothenic acid and biotin; amino acids, e.g. methionine, cysteine, cystine and tyrosine; bacteriocides, e.g. salicylic acid, hinokitiol, resorcin, trichlorocarbanilide and isopropylmethylphenol; hormones, e.g. ethynylestradiol and progesterone; and extracts, e.g. those extracted from seaweeds, aloe, jujube and sesame seeds. These additional components are incorporated into the composition preferably in an amount of 0.0001 to 3% based on the total weight of the composition.

Moreover, other materials commonly contained in cosmetics can also be incorporated into the composition. Examples of them include oils, humectants, lower alcohols, thickening agents, antioxidants, chelating agents, agents for imparting good feeling upon application, pH-adjusting agents, preservatives, perfumes and colorants. Examples of the oils include fats and oils such as olive oil, jojoba oil and hydrogenated oils; waxes such as spermaceti, beeswax and lanolin; hydrocarbons such as liquid paraffin, ceresin and squalane; fatty acids such as capric acid, lauric acid, myristic acid, palmitic acid, stearic acid, isomyristic acid, isostearic acid, adipic acid, sebacic acid, caproleic acid, lauroleic acid, palmitoleic acid, oleic acid, ricinoleic acid, linoleic acid and linolenic acid; alcohols such as cetanol, stearyl alcohol, lanolin alcohol and hexyldecanol; and fatty acid esters such as hexyl laurate, isopropyl myristate, butyl myristate, octyldodecyl myristate, isopropyl palmitate, isocetyl stearate, ethyl isostearate, diisopropyl adipate, diethyl sebacate, ethyl oleate, isopropyl linolenate, methyl linolenate and methyl ricinoleate. These oils are incorporated into the composition for hair in an amount of preferably 0.5 to 85%, based on the composition. Examples of the humectants include glycerol, 1,3-butylene glycol, propylene glycol, dipropylene glycol, ethylene glycol, sodium pyrrolidonecarboxylate and N-methyl-2-pyrrolidone. Examples of the lower alcohols include ethanol and isopropanol. Examples of the agents for imparting good feeling to users include l-menthol and benzyl nicotinate. Examples of the thickening agents include polyethylene glycol and sodium carboxymethyl cellulose. Examples of the antioxidants include dibutylhydroxytoluene, butylhydroxyanisole and propyl gallate. Examples of the chelating agents include disodium edetate and ethanehydroxy diphosphate. Examples of the pH-adjusting agents include citric acid, sodium citrate, boric acid, borax and disodium hydrogen phosphate. Examples of the preservatives include methyl p-hydroxybenzoate, ethyl p-hydroxybenzoate, dehydroacetic acid, salicylic acid and benzoic acid. The optional components are not restricted to those listed above. The composition for hair can be prepared by appropriately mixing the foregoing essential components and optional components. It can be used in any form suitable for the external use such as a hair tonic type-alcoholic pharmaceutical preparation, cream, lotion, milky lotion or ointment.

An example of the hair tonic-type alcoholic preparations comprises 0.01 to 2% of the component [A], 0.3 to 10% of the component [B], 10 to 98% of the lower alcohol, 0 to 3% of the pharmaceutical component, 0 to 15% of the humectant, 1 to 85% of purified water, based on the total weight of the composition and if necessary, a very small amount of a perfume. An example of the hair creams comprises 0.01 to 2% of the component [A], 0.3 to 10% of the component [B], 20 to 80% of the oil, 0 to 15% of the humectant, 15 to 80% of purified water, based on the total weight of the composition and if necessary, very small amounts of the preservative and perfume. An example of the milky lotions comprises 0.01 to 2% of the component [A], 0.3 to 10% of the component [B], 5 to 30% of the oil, 0 to 15% of the humectant, 50 to 95% of purified water, based on the total weight of the composition and if necessary, very small amounts of the preservative and perfume.

When the composition of the present invention is in liquid form, it can be placed in a pressure vessel together with an ordinary propellant, carbon dioxide gas, oxygen gas or LPG.

Although the details of the mechanism of the prevention of graying of hair or restoring grayed hair to its natural color with the cAMP compound used in the present invention has not yet been elucidated, it is assumed that, when it is externally applied, the melanocytes present in the scalp radix pili and melanoblasts which are precursor cells of the melanocytes are activated to promote the formation of melanin and the resultant melanin granules are incorporated into mother cells of hair. It is supposed that the effective component [A] of the present invention exhibits the above-described excellent effect which has never been obtained, since this component has a far more excellent absorbability through the scalp and melanin-formation activity than those of cAMP compound heretofore used. By using the component [A] in combination with the component [B], the absorbability of the component [A] through the scalp is remarkably improved to exhibit a further improved effect.

The level of safety of the cAMP compounds used in the invention was checked to find no practical problem with respect to acute toxicity and skin irritation, and thus a high level of safety thereof was confirmed.

No problem of safety was posed by the combination of the component [A] with the component [B].

Thus according to the present invention, a practically valuable composition for preventing graying of hair and restoring grayed hair to its natural color upon externally applied to the scalp is provided.

Therefore, the composition of the present invention can be widely used in various forms capable of being externally applied to the scalp. Such forms include, for instance, toilet waters, hair tonic-type alcoholic preparations, creams, lotions, milky lotions, ointments, hair treatments and hair conditioners. In this connection, it is preferable that the composition be applied to a human scalp in an amount of 1–100 mg/cm$^2$ per day.

The following Examples will further illustrate the present invention.

[Examples]

Example 1

The absorbability through the skin is one of the characteristic properties relating to the biological availability of active components. The absorption of samples through the skin was measured in vitro by the following method to evaluate the effect thereof.

The skin of the back of each of male Hartley guineapigs was taken and it was fixed between a donor and a reservoir of a vertical diffusion cell in such a way that the epidermis is on the upper side.

Then the vessel on the reservoir side was filled with Ringer's solution. It was kept at 37° C. under stirring. 50 mg of a composition shown below was applied to the skin on the donor side. A part of the Ringer's solution was taken as a sample at certain time intervals and the quantity of the cAMP derivative in the Ringer's solution was determined according to high-performance liquid chromatography. The absorbability of the cAMP derivative in the composition through the skin was evaluated in terms of the permeability thereof through the skin.

The results obtained after the 24 h determination are shown in Table 2.

The results are shown in terms of the relative permeability of the component [A] alone or that of the combination of the component [A] with the component [B] where the permeability of sodium salt of cAMP derivative is indicated as 1.

| Common composition: | |
|---|---|
| Component [A]: | 1.0% |
| Component [B]: | 2.0% |
| 95% (v/v) Ethanol: | 70% |
| Purified water: | balance. |

In Table 2, POE represents polyoxyethylene and the numerals in the parentheses represent the average molar number of added ethylene oxide (the same shall apply hereinafter).

TABLE 2

| | Component [A] | Component [B] | Relative absorbability through skin |
|---|---|---|---|
| Comp. Ex. | Na $N^6,O^2$ dibutyryl-cAMP (Comp. Ex.) | — | 1 |
| Present invention | $N^6,O^2$-dibutyryl-cAMP 2-amino-2-methyl-1-propanol salt | — | 3.9 |
| | (Compound No. 9 in Table 1) | Sodium POE(5) cetyl ether phosphate | 20 |
| Comp. Ex. | Na 8-methoxy-cAMP (Comp. Ex.) | — | 1 |
| | 8-Methoxy-cAMP mono-ethanol-amine salt (Comp. Ex.) | — | 0.7 |
| | 8-Methoxy-cAMP triethanol-amine salt (Comp. Ex,) | — | 0.6 |
| | 8-Methoxy-cAMP tris(hydroxymethyl)amino-methane salt (Comp. Ex.) | — | 1.1 |
| Present invention | 8-Methoxy-cAMP 2-amino-2-methyl-1,3-propanediol salt (Compound No. 53 in Table 1) | POE (15) stearyl ether (HLB 12) | 4.5 24 |
| Comp. Ex. | Na 1,$N^6$-Etheno-cAMP (Comp. Ex.) | — | 1 |
| | 1,$N^6$-Etheno-cAMP 2-amino-2-methyl-1,3-propanediol salt (Compound No. 82 in Table 1) | POE (10) mono-stearate (HLB 11) | 3.5 17 |

It will be understood from the results shown in Table 2 that 2-amino-2-methyl-1-propanol salt and 2-amino-2-methyl-1,3-propanediol salt of cAMP derivative, i.e. the active component of the present invention, have a far more excellent absorbability through the skin than that of most common sodium salt or organic salts such as monoethanolamine salt, triethanolamine salt and tris(-hydroxymethyl)aminomethane salt used in Comparative Examples and that when the component [A] is used in combination with the component [B], the absorbability through the skin can be further improved.

Example 2

The melanin-forming activity of the active component [A] of the present invention was evaluated by the following method.

It is known that although pheomelanin (yellow melanin) is usually formed in the bulbus pili of yellow mice, Eumelanin (black melanin) is formed under the influence of a substance which promotes the melanin formation. The Eumelanin-forming activity of the active component [A] of the present invention was evaluated using the yellow mice.

In the experiment, the skin of the back of each yellow mouse was taken and cut into small pieces. They were cultured in a liquid medium containing 0.4% (v/v) of each composition for 48 h. Then the reaction was stopped with 10% formalin. The pieces were dehydrated and made transparent by ordinary methods. Then they were sealed in balsam to form samples.

The melanin-formation in the bulbus pili in the skin pieces was microscopically observed and the ratio of the Eumelanin-forming bulbus pili to the total bulbus pili was calculated. The results are shown in Table 3.

The results are shown in terms of the relative melanin-forming activity of the active component [A] of the present invention where the melanin-forming activity of sodium salt of cAMP derivative is indicated as 1.

| Common composition: | |
|---|---|
| Component [A]: | 1% |
| 95% (v/v) Ethanol: | 50% |
| Purified water: | balance |

TABLE 3

| | Component [A] | Melanin-forming activity (relative activity) |
|---|---|---|
| Comp. Ex. | Na $N^6,O^{2'}$-Dibutyryl-cAMP | 1 |
| Present invention | $N^6,O^{2'}$-dibutyryl-cAMP 2-amino-2-methyl-1,3-propanediol salt (compound No. 46 in Table 1) | 2.1 |
| Comp. Ex. | Na 8-methoxy-cAMP | 1 |
| Present invention | 8-Methoxy-cAMP 2-amino-2-methyl-1,3-propanediol salt (compound No. 53 in Table 1) | 2.8 |
| Comp. Ex. | Na 8-Ethoxy-cAMP | 1 |
| Present invention | 8-Ethoxy-cAMP 2-amino-2-methyl-1-propanol salt (compound No. 17 in Table 1) | 2.6 |
| Comp. Ex. | Na 8-Benzylthio-cAMP | 1 |
| Present invention | 8-Benzylthio-cAMP 2-amino-2-methyl-1,3-propanediol salt (compound No. 70 in Table 1) | 2.2 |
| Comp. Ex. | Na 1,$N^6$-Etheno-cAMP | 1 |
| Present invention | 1,$N^6$-Etheno-cAMP 2-amino-2-methyl-1-propanol salt (compound No. 75 in Table 1) | 1.9 |

It will be understood from the results shown in Table 3 that 2-amino-2-methyl-1-propanol salt and 2-amino-2-methyl-1,3-propanediol salt of cAMP derivative, i.e. active components of the present invention, have a far higher melanin-forming activity than that of sodium salts of corresponding derivatives used in Comparative Examples.

The above-described results suggest that the active component of the present invention has not only excellent absorbability through the scalp but also excellent melanin-forming activity.

Example 3

Components 3,4 and 6 to 8 was homogeneously dissolved in component 1 shown in Table 4. Separately, components 2 and 5 were added to component 9 to form a homogeneous solution, to which the above-described ethanol solution of components 3, 4 and 6 to 8 was added to prepare a hair tonic-type composition for hair.

The composition is shown in Table 4 in which the amounts are given by % by weight (the same shall apply hereinafter).

TABLE 4

| | Component | Present invention | Comp. Ex. |
|---|---|---|---|
| 1 | 95% (v/v) Ethanol | 80.0 | 80.0 |
| 2 | 8-Methoxy-cAMP 2-amino-2-methyl-1,3-propanediol salt (compound No. 53 in Table 1) | 0.1 | — |
| 3 | POE (20) lauryl ether (HLB 16) | 2.0 | 2.0 |
| 4 | Isopropyl myristate | 1.5 | 1.5 |
| 5 | Sodium pyrrolidonecarboxylate | 1.0 | 1.0 |
| 6 | l-menthol | 0.1 | 0.1 |
| 7 | Biotin | 0.001 | 0.001 |
| 8 | Perfume | very small amount | very small amount |
| 9 | Purified water | balance | balance |

The composition for hair thus prepared was applied to the scalp of 12 male and female subjects (37 to 53 years old) having grayed hair according to Half-Head method wherein the composition of the present invention and that of the Comparative Example were applied to the right half of the scalp and the left half thereof, respectively, twice a day (in the morning and at night) for 3 months. Then the effects of preventing graying of hair and restoring grayed hair to its natural color were evaluated by comparing the conditions of the portions before and after the application. The results are shown in the following Table 5:

TABLE 5

| Composition of the present invention was better | Composition of the present invention was slightly better | Equivalent | Composition of the Comparative Example was slightly better | Composition of the Comparative Example was better |
|---|---|---|---|---|
| 6 | 4 | 2 | 0 | 0 |

The results shown in Table 5 reveals that the composition for hair of the present invention containing 8-methoxy-cAMP 2-amino-2-methyl-1,3-propanediol salt had more excellent effect of reducing the amount of grayed hair than that of the composition free from 8-methoxy cAMP 2-amino-2-methyl-1,3-propanediol salt and thus had remarkable effects of preventing graying of hair and restoring grayed hair to its natural color.

In addition, during and after the application of the composition of the present invention for 3 months, no abnormal symptoms of the scalp were observed.

Example 4

Components 3, 4 and 6 to 8 were homogeneously dissolved in component 1 shown in Table 6. Separately, components 2 and 5 were added to component 9 to form a homogeneous solution, to which the above-described ethanol solution of components 3, 4 and 6 to 8 was added to prepare a hair tonic-type composition for hair. The composition is shown in Table 6.

TABLE 6

| Component | Present invention | Comp. Ex. |
|---|---|---|
| 1 95% (v/v) Ethanol | 90 | 90 |
| 2 8-Benzylthio-cAMP 2-amino-2-methyl-1-propanol salt (Compound No. 33 in Table 1) | 0.2 | — |
| 3 Sodium POE (10) cetyl ether phosphate | 1.5 | 1.5 |
| 4 Oleic acid | 2.0 | 2.0 |
| 5 Sodium pyrrolidonecarboxylate | 1.5 | 1.5 |
| 6 D,L-tocopherol | 0.01 | 0.01 |
| 7 Antioxidant | very small amount | very small amount |
| 8 Perfume | very small amount | very small amount |
| 9 Purified water | balance | balance |

The composition for hair thus prepared was applied to the scalp of 12 male and female subjects (39 to 55 years old) having grayed hair according to Half-Head method wherein the composition of the present invention and that of the Comparative Example were applied to the right half of the scalp and the left half thereof, respectively, twice a day (in the morning and at night) for 3 months. Then the effects of preventing graying of hair and restoring grayed hair to its natural color were evaluated by comparing the conditions of the portions before and after the application. The results are shown in the following Table 7:

TABLE 7

| Composition of the present invention was better | Composition of the present invention was slightly better | Equivalent | Composition of the Comparative Example was slightly better | Composition of the Comparative Example was better |
|---|---|---|---|---|
| 5 | 4 | 3 | 0 | 0 |

Table 7 reveals that the composition for hair of the present invention containing 8-benzylthio-cAMP 2-amino-2-methyl-1-propanol salt had more excellent effect of reducing the amount of grayed hair than that of the composition free from 8-benzylthio cAMP 2-amino-2-methyl-1-propanol salt and thus had remarkable effects of preventing graying of hair and restoring grayed hair to its natural color.

In addition, during and after the application of the composition of the present invention for 3 months, no abnormal symptoms of the scalp were observed.

Example 5

Hair tonic-type compositions for hair were prepared in the same manner as that of Example 4 except that 8-benzylthio-cAMP 2-amino-2-methyl-1-propanol salt was replaced with 8-hydroxy-cAMP 2-amino-2-methyl-1,3-propanediol salt (Compound No. 52 in Table 1), 8-ethoxy-cAMP 2-amino-2-methyl-1,3-propanediol salt (Compound No. 54 in Table 1), 8-butoxy-cAMP 2-amino-2-methyl-1,3-propanediol salt (Compound No. 55 in Table 1) or 8-ethylhydroxythio-cAMP 2-amino-2-methyl-1,3-propanediol salt (Compound No. 64 in Table 1). After the evaluation conducted in the same manner as that of Example 4, it was found that their effects of preventing graying of hair and restoring grayed hair to its natural color were substantially equivalent to those obtained in Example 4.

Example 6

Components 1 to 6 shown in table 8 were dissolved by heating at 70° C. Separately, Components 7 to 14 were also dissolved by heating at 70° C. to obtain a solution, to which the above-described oil phase solution of Components 1 to 6 was added to form an emulsion. The emulsion was cooled to room temperature. In the course of the cooling, Component 15 was added thereto to prepare an emulsion-type composition for hair as shown in Table 8. They all had excellent effects of preventing graying of hair and restoring grayed hair to its natural color.

TABLE 8

| Component | Present invention I | II | III |
|---|---|---|---|
| 1 Liquid paraffin (#70) | 10.0 | 10.0 | 10.0 |
| 2 Isopropyl isostearate | 2.0 | 2.0 | 2.0 |
| 3 Sorbitan sesquioleate (HLB 5) | 0.5 | 0.5 | 0.5 |
| 4 Stearic acid | 2.0 | 2.0 | 2.0 |
| 5 POE (20) stearyl ether (HLB 14) | 0.7 | 0.7 | 0.7 |
| 6 Butyl p-hydroxybenzoate | 0.1 | 0.1 | 0.1 |
| 7 $N^6,O^{1'}$-dibutyryl-cAMP 2-amino-2-methyl-1,3-propanediol salt (Compound No. 46 in Table 1) | 0.5 | — | — |
| 8 8-Methoxy-cAMP 2-amino-2-methyl-1,3-propanediol salt (Compound No. 53 in Table 1) | — | 0.5 | — |
| 9 1,$N^6$-Etheno-cAMP 2-amino-2-methyl-1-propanol salt (Compound No. 75 in Table 1) | — | — | 0.5 |
| 10 Glycerol | 2.0 | 2.0 | 2.0 |
| 11 Carbopol 941* | 0.1 | 0.1 | 0.1 |
| 12 Ethanol | 10.0 | 10.0 | 10.0 |
| 13 Methyl p-hydroxybenzoate | 0.1 | 0.1 | 0.1 |
| 14 Purified water | balance | balance | balance |
| 15 Perfume | very small amount | very small amount | very small amount |

*Carboxyvinyl polymer (molecular weight: 1,000,000 to 1,500,000)

Example 7

The absorption of samples through the skin was measured in vitro by the same manner as Example 1. The results are shown in Table 9 in terms of the relative permeability of component [A] alone or that of the combination of component [A] with component [B] where the permeability of sodium salt of cAMP derivative is indicated as 1.

| Common Composition: | |
|---|---|
| Component [A]: | 1.0% |
| 95% (V/V) Ethanol: | 20.0% |
| purified water: | balance |

TABLE 9

| | Component [A] | Component [B] | Relative absorbability through skin |
|---|---|---|---|
| Comp. Ex. | $N^6,O^{2'}$-dibutyryl-cAMP.Na | — | 1 |
| Present invention | $N^6,O^{2'}$-dibutyryl-cAMP 2-amino-1-propanol salt | — | 1.9 |
| | — | POE(10)cetyl ether (2%) (HLB:11) | 22 |
| Comp. Ex. | 8-methoxy-cAMP.Na | — | 1 |
| Present invention | 8-methoxy-cAMP lysine salt | — | 3.0 |
| | | POE(15)stearyl ether (3%) (HLB:12) | 32 |
| Comp. Ex. | 8-hydroxy-cAMP.Na | — | 1 |
| Present invention | 8-hydroxy-cAMP histidine salt | — | 2.2 |
| | | sodium POE(10) lauryl ether phosphate (4%) | 29 |
| Comp. Ex. | $1,N^6$-etheno-cAMP.Na | — | 1 |
| Present invention | $1,N^6$-etheno-cAMP methylamine salt | — | 2.6 |
| | | Sorbitan Sesquioleate (1%) POE(50) hardening castor oil (4%) (HLB:11.5) | 18 |
| Comp. Ex. | 8-butylamino-cAMP.Na | — | 1 |
| Present invention | 8-butylamino-cAMP 2-amino-1-hexanol salt | — | 2.0 |
| | | POE(20)stearyl ether (2%) (HLB:14) | 25 |

The result shown in Table 9 reveals that 2-amino-1-propanol salt, 2-amino-1-hexanol salt, lysine salt, histidine salt and methylamine salt of cAMP derivatives according to the present invention has higher absorbability through the skin than that of sodium salts of comparative examples and that the combination of said salt and component [B] further improves the absorbability of the salt through the skin.

What is claimed is:

1. A method for preventing graying of hair and restoring grayed hair to its natural color by applying to a human scalp an effective amount of a composition consisting essentially of a salt of formula I or II set forth below and an inert carrier wherein the concentration of said salt ranges from about 0.001 to 5% by weight, based on the total weight of the composition:

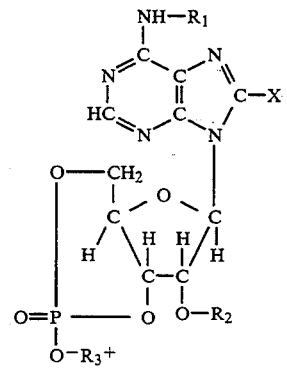

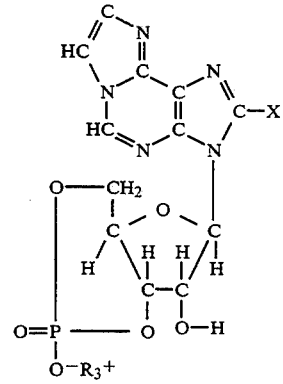

wherein $R_1$ and $R_2$ each represent a hydrogen atom or an acyl group having 1 to 12 carbon atoms, X represents a hydrogen atom, an O-containing group, an S-containing group, an alkylamino group having 1 to 12 carbon atoms or a halogen atom, and $R_3^+$ represents an ammonium cation derived from 2-amino-2-methyl-1,3-propanediol, 2-amino-alkanol having 3 to 6 carbon atoms, monoalkylamine having 1 to 3 carbon atoms, lysine or histidine.

2. The method of claim 1, wherein said composition for hair comprises:
   (a) a compound according to claim 1
   (b) a nonionic surfactant having an HLB in the range of 3 to 19 or a polyoxyethylene alkyl ester phosphate anionic surfactant, and
   (c) an inert carrier.

3. The method of claim 2, wherein said nonionic surfactant is a polyoxyethylene ether of a higher alcohol having 8 to 24 carbon atoms and which has an average addition molar number of ethylene oxides of 2 to 40.

4. The method of claim 2, wherein said polyoxyethylene alkyl ester phosphate anionic surfactant is a sodium phosphate salt of a polyoxyethylene derivative of a higher alcohol having 12 to 18 carbon atoms and which has an average addition molar number of ethylene oxides of 1 to 20.

5. The method of claim 2, wherein the concentration of said nonionic surfactant or polyoxyethylene alkyl ester phosphate anionic surfactant is about 0.1 to 20% by weight, based on the total weight of the composition.

6. The method of claim 2, wherein the weight ratio of component (a) to component (b) is 1/2000 to 50/1.

7. The method of claim 2, which the composition further contains an oil and/or a humectant.

8. The method of claim 1, wherein said effective amount when applied daily to the human scalp is an amount of said composition which provides for about 1 to 100 mg per cm² area of the human scalp.

9. The method of claim 1, wherein said composition is in the form of a hair tonic alcoholic preparation which comprises 0.01 to 2% by weight of component (a), 0.3 to 10% by weight of component (b), 10 to 98% by weight of a lower alcohol, 0 to 3% by weight of a pharmaceutical component, 0 to 15% by weight of a humectant, 1 to 85% by weight of purified water, based on the total weight of the composition.

10. The method of claim 1, wherein said composition is in the form of a hair cream which comprises 0.01 to 2% by weight of component (a), 0.3 to 10% by weight of component (b), 20 to 80% by weight of an oil, 0 to 15% by weight of a humectant, 15 to 80% by weight of purified water, based on the total weight of the composition.

11. The method of claim 1, wherein said composition is in the form of a milky lotion which comprises 0.01 to 2% by weight of component (a), 0.3 to 10% by weight of component (b), 5 to 30% by weight of an oil, 0 to 15% by weight of a humectant, 50 to 95% by weight of purified water, based on the total weight of the composition.

* * * * *